United States Patent
Davies

(10) Patent No.: US 7,851,488 B2
(45) Date of Patent: *Dec. 14, 2010

(54) TETRAHYDROPYRIDINES WITH CENTRAL NERVOUS SYSTEM ACTIVITY

(75) Inventor: Huw M. L. Davies, E. Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 616 days.

This patent is subject to a terminal disclaimer.

(21) Appl. No.: 11/716,852

(22) Filed: Mar. 12, 2007

(65) Prior Publication Data

US 2007/0232634 A1   Oct. 4, 2007

Related U.S. Application Data

(60) Provisional application No. 60/781,245, filed on Mar. 10, 2006.

(51) Int. Cl.
| | | |
|---|---|---|
| *A01N 43/40* | (2006.01) | |
| *A61K 31/445* | (2006.01) | |
| *C07D 211/00* | (2006.01) | |
| *C07D 295/00* | (2006.01) | |
| *C07D 211/30* | (2006.01) | |
| *C07D 211/20* | (2006.01) | |

(52) U.S. Cl. .................. 514/317; 546/184; 546/248
(58) Field of Classification Search .................. 514/317; 546/184, 248
See application file for complete search history.

(56) References Cited

U.S. PATENT DOCUMENTS

| 5,227,385 A | 7/1993 | Caldwell et al. |
| 5,262,428 A | 11/1993 | Davies et al. |
| 5,288,872 A | 2/1994 | Davies et al. |
| 5,342,949 A | 8/1994 | Davies et al. |
| 5,591,854 A | 1/1997 | Davies |
| 5,760,055 A | 6/1998 | Davies |
| 5,763,455 A | 6/1998 | Davies et al. |
| 5,849,765 A | 12/1998 | Curtis et al. |
| 6,008,227 A | 12/1999 | Davies et al. |
| 6,013,242 A | 1/2000 | Davies et al. |

OTHER PUBLICATIONS

Davies et al., Synthesis of methylphenidate analogues and their binding affinities at dopamine and serotonin transport sites. Bioorganic & Medicinal Chemistry Letters 14 (2004), pp. 1799-1802.

Davies et al., New Strategic Reactions for Organic Synthesis: Catalytic Asymmetric C-H Activation α to Nitrogen as a Surrogate for the Mannich Reaction. Journal of the American Chemical Society, 2003, V. 125, No. 21, pp. 6462-6468.

Davies, et al.; Highly Regio-, Diastereo-, and Enantioselective C—H Insertions of Methyl Aryldiazoacetates into Cyclic N-Boc-Protected Amines. Asymmetric Synthesis of Novel $C_2$-Symmetric Amines and *threo*-Methylphenidate; J. American Chemical Society 1999, vol. 121; pp. 6509-6510.

*Primary Examiner*—Sreeni Padmanabhan
*Assistant Examiner*—Sarah Pihonak
(74) *Attorney, Agent, or Firm*—Hodgson Russ LLP

(57) ABSTRACT

Provided are novel tetrahydropyridine derivatives bearing substituents. These compounds can be used for alleviating the symptoms of CNS disorders.

12 Claims, 1 Drawing Sheet

| Ar | Rh(II) | yield, % | de, % | ee, % | product |
| --- | --- | --- | --- | --- | --- |
| 4-BrC6H4 | Rh2(S-DOSP)4 | 70 | 82 | 95 | (2S,2'R)-4b |
|  | Rh2(R-DOSP)4 | 73 | >80 | 94 | (2R,2'S)-4b |
|  | Rh2(R/S-DOSP)4 | 71 | 82 | <5 | (±)-4b |
| 4-ClC6H4 | Rh2(S-DOSP)4 | 61 | 79 | 95 | (2S,2'R)-4c |
|  | Rh2(R-DOSP)4 | 58 | 74 | 95 | (2R,2'S)-4c |
|  | Rh2(R/S-DOSP)4 | 54 | 71 | <5 | (±)-4c |
| 3,4-Cl2C6H3 | Rh2(S-DOSP)4 | 56 | 55 | 80 | (2S,2'R)-4d |
|  | Rh2(R-DOSP)4 | 53 | 61 | 81 | (2R,2'S)-4d |
|  | Rh2(R/S-DOSP)4 | 55 | 61 | <5 | (±)-4d |
| 2-naphthyl | Rh2(S-DOSP)4 | 67 | 64 | 70 | (2S,2'R)-4e |
|  | Rh2(R-DOSP)4 | 64 | 60 | 65 | (2R,2'S)-4e |
|  | Rh2(R/S-DOSP)4 | 61 | 57 | <5 | (±)-4e |
| 4-PhC6H4 | Rh2(S-DOSP)4 | 74 | 71 | 94 | (2S,2'R)-4f |
|  | Rh2(R-DOSP)4 | 75 | 70 | 91 | (2R,2'S)-4f |
|  | Rh2(R/S-DOSP)4 | 74 | 72 | <5 | (±)-4f | ns

TETRAHYDROPYRIDINES WITH CENTRAL NERVOUS SYSTEM ACTIVITY

This application claims priority to U.S. Patent Application Ser. No. 60/781,245, filed on Mar. 10, 2006, the entire disclosure of which is incorporated herein by reference.

This work was supported by Grant Nos. NO1 DA-18826 and 5R01DA15225-03 from the National Institutes of Health. The Government has certain rights in the invention.

FIELD OF THE INVENTION

The present invention relates to tetrahydropyridine compounds having central nervous system activity.

BACKGROUND OF THE INVENTION

Central Nervous System disorders are economically and socially devastating. For example, schizophrenia is one of the leading causes of disability worldwide with a lifetime prevalence of 0.6 to 1.3% characterized by high morbidity and mortality. Only less than 15% of people with this disability are competitively employed, whilst about 20% live independently.

Schizophrenia is generally characterized by positive symptoms (such as delusions, hallucinations, disorganized behavior), negative symptoms (such as anergia), affective symptoms (such as dysphoria, hopelessness, anxiety, hostility, aggression) and/or cognitive deficits.

Typical treatment for such disorders includes drugs that affect the monanine receptor systems. For example, the primary effect of first generation antipsychotics is dopamine (D2 receptor) blockade. While these are effective in treating the positive symptoms of schizophrenia, they exert modest effects on negative symptoms and cognitive deficits. Thus, despite the availability of some drugs for treating central nervous system disorders such as schizophrenia, there are many unmet needs for improved methods and compounds for treating central nervous system disorders.

SUMMARY OF THE INVENTION

The present invention provides compositions having the general structure:

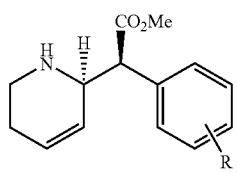

where R represents one or more substituents, such as hydrogen, substituted or unsubstituted phenyls, halogens, and/or adjacent rings which share a side with the R-bearing aryl group. These compounds can be used for alleviating the symptoms of central nervous system disorders.

DETAILED DESCRIPTION OF THE INVENTION

Figure 1:
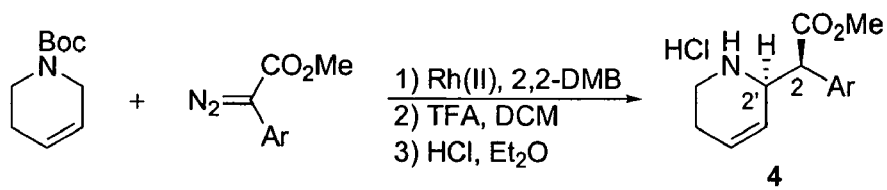
FIG. 1 provides a summary of examples of the compounds of the invention.

The present invention provides tetrahydropyridines which can function as monoamine transporter inhibitors, and therefore have utility as selective serotonin transporter (SERT) inhibitors. Without intending to be bound by any particular structural classification, it is considered that the compounds are generally related to Ritalin.

These compounds may be administered orally, parenterally, intramuscularly, intravenously, mucosally or by other route. In one embodiment, the route of administration is oral. The dosage regimen of these compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg.

Other ingredients may be added to the compounds as part of a pharmaceutical composition depending on the dosage form, particular needs of the patient, and method of manufacture, among other things. Examples include but are not limited to binders, lubricants, fillers, flavorings, preservatives, colorings, diluents, etc. The selection of particular substances and their compatibilities with the compositions of the present invention can be readily ascertained by those of ordinary skill in the art. Details are also provided in U.S. Pat. No. 5,763,455, which is incorporated herein by reference.

Threo-Methylphenidate (1) in its racemic form is sold under the trade-name Ritalin. This invention describes the potential use of erythro unsaturated structures (2) related to Ritalin as therapeutic agents for neuropsychiatric diseases.

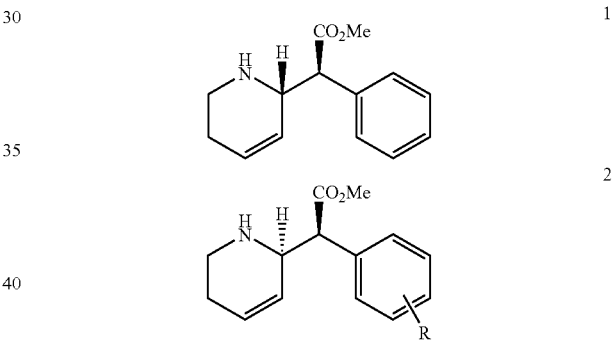

We have found that compounds of formula 2, above, can show favorable biological activity. Accordingly, the compounds of the present invention have the following general structure:

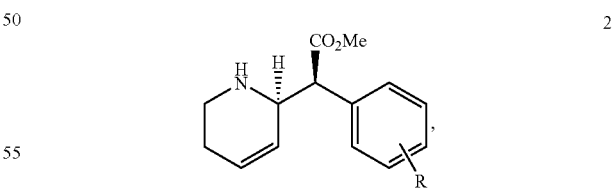

its enantiomer, threo-diastereomer (where the structure is as shown except the dashed bond between the hydrogen and the pyridine ring is directed out of the page instead of into the page) or racemic or diastereomeric mixtures thereof. R can be such that the R-bearing ring is mono-, di- or tri-substituted, and in which the substituents consist of hydrogen, alkyl, alkenyl, alkoxy, halo, nitro, cyano, keto, amino, carboxylate, or a combination thereof. Preferably R represents one or more substituents selected from the group consisting of hydrogen, substituted or unsubstituted phenyls, halogens, and adjacent rings which share a side with the R-bearing phenyl group.

Preferred are substituents such as hydrogen, unsubstituted phenyls, one or more chlorines, bromine, and single adjacent aromatic rings which, together with the R-bearing ring, comprise a naphthyl group.

More preferred are R-groups in the para-position of the R-bearing ring, such as an unsubstituted phenyl in the para position on the R-bearing ring; chlorine substituents at either or both the meta and/or para positions, a bromine substituent at the para position; and one adjacent ring such that, together with the R-bearing ring, it comprises a para-2-naphthyl group. In one embodiment, compound 2 has the structure:

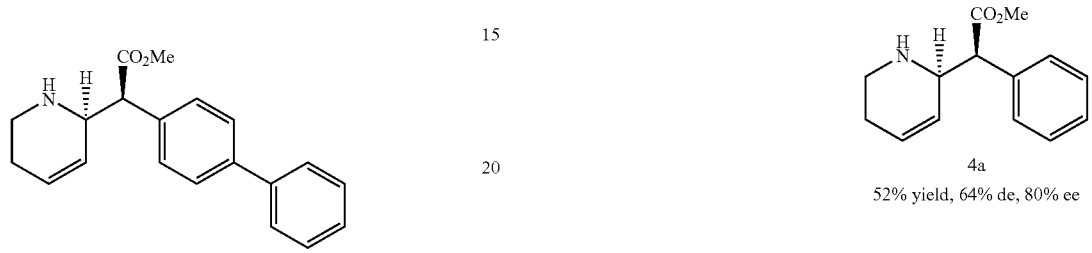

While the present invention is illustrated by way of the following examples, the examples are meant only to illustrate particular embodiments of the present invention and are not meant to be limiting in any way.

EXAMPLE 1

This Example describes the synthesis of compounds of the invention. In one embodiment, we synthesized N-Boc-tetrahydropyridine (4a) by a C—H activation step. This reaction preferentially forms the eyrthro product with reasonably high diastereo- and enantioselectivity.

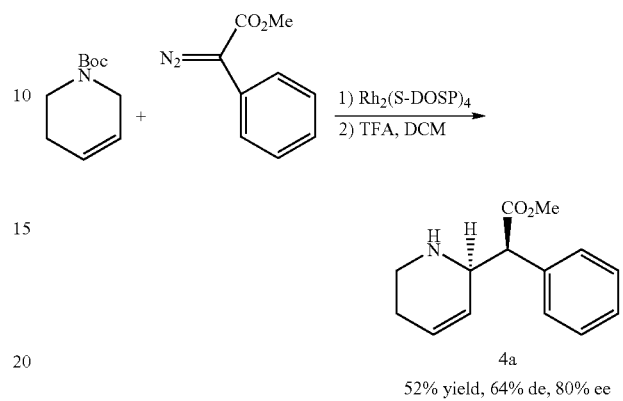

4a
52% yield, 64% de, 80% ee

The synthesis of the tetrahydropyridines was achieved using the general procedure shown above. A variety of methyl aryldiazoacetates were reacted with N-Boc-tetrahydropyridine. The diastereoselectivity of the products range from 57-82% de, and the enantioselectivites were 65-95% ee. Reaction of methyl aryldiazoacetates with N-Boc-tetrahydropyridine to obtain examples of compounds of the invention is shown in Table 1.

TABLE 1

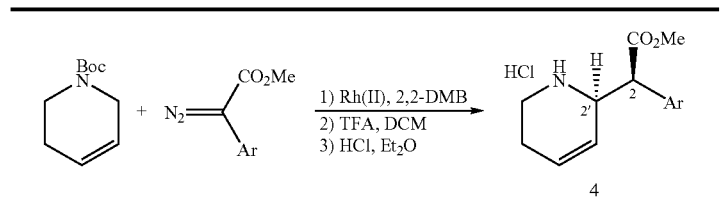

| Ar | Rh(II) | yield, % | de, % | ee, % | product |
|---|---|---|---|---|---|
| 4-Br-C6H4 | $Rh_2(S-DOSP)_4$ | 70 | 82 | 95 | (2S,2'R)-4b |
|  | $Rh_2(R-DOSP)_4$ | 73 | >80 | 94 | (2R,2'S)-4b |
|  | $Rh_2(R/S-DOSP)_4$ | 71 | 82 | <5 | (±)-4b |
| 4-Cl-C6H4 | $Rh_2(S-DOSP)_4$ | 61 | 79 | 95 | (2S,2'R)-4c |
|  | $Rh_2(R-DOSP)_4$ | 58 | 74 | 95 | (2R,2'S)-4c |
|  | $Rh_2(R/S-DOSP)_4$ | 54 | 71 | <5 | (±)-4c |
| 3,4-Cl2-C6H3 | $Rh_2(S-DOSP)_4$ | 56 | 55 | 80 | (2S,2'R)-4d |
|  | $Rh_2(R-DOSP)_4$ | 53 | 61 | 81 | (2R,2'S)-4d |
|  | $Rh_2(R/S-DOSP)_4$ | 55 | 61 | <5 | (±)-4d |

TABLE 1-continued

| Ar | Rh(II) | yield, % | de, % | ee, % | product |
|---|---|---|---|---|---|
| naphthalen-2-yl | Rh$_2$(S-DOSP)$_4$ | 67 | 64 | 70 | (2S,2'R)-4e |
|  | Rh$_2$(R-DOSP)$_4$ | 64 | 60 | 65 | (2R,2'S)-4e |
|  | Rh$_2$(R/S-DOSP)$_4$ | 91 | 57 | <5 | (±)-4e |
| 4-biphenyl | Rh$_2$(S-DOSP)$_4$ | 74 | 71 | 94 | (2S,2'R)-4f |
|  | Rh$_2$(R-DOSP)$_4$ | 75 | 70 | 91 | (2R,2'S)-4f |
|  | Rh$_2$(R/S-DOSP)$_4$ | 74 | 72 | <5 | (±)-4f |

The following are representative experimental procedures for synthesizing compounds of the invention.

(S)-Methyl 2-(4-bromophenyl)-2-((R)-1,2,5,6-tetrahydropyridin-2-yl)acetate hydrochloride ((2S,2'R)-4a)

Methyl 4-bromo-phenyldiazoacetate (418 mg, 1.6 mmol) in 2,2-dimethylbutane (10 mL) and toluene (4 mL) was added dropwise over 3.5 h using a syringe pump to a solution of Rh$_2$(S-DOSP)$_4$ (31 mg, 0.016 mmol) and tert-butyl 5,6-dihydropyridine-1(2H)-carboxylate (150 mg, 0.82 mmol) in 2,2-dimethylbutane (10 mL). After the addition was complete, the reaction was stirred for 1 h at 23° C. The solvent was removed under reduced pressure and the residue was redissolved in DCM (15 mL). TFA (0.3 mL, 4.1 mmol) was added and the reaction was stirred for 16 h. The solvent was removed under reduced pressure and the residue was dissolved in Et$_2$O (30 mL), extracted with 10% HCl (3×15 mL). The combined aqueous layers were basified to pH 8-9 (NaHCO$_3$, 1M NaOH) and extracted with EtOAc (3×30 mL). The combined EtOAc layers were washed with water (30 mL) and brine (30 mL), then dried over Na$_2$SO$_4$. The solvent was removed under reduced pressure and a diastereoselectivity of 82% was obtained (as determined by $^1$H NMR of the crude reaction mixture). The residue was purified by flash chromatography (SiO$_2$, Et$_2$O/Pentane/TEA=50/50/2) to give the free amine. The free amine was then dissolved in Et$_2$O (20 mL) and HCl (1M in Et$_2$O, 5 eq) was added. The reaction was stirred for 1 h then the solvent was removed under reduced pressure to give the title compound (2S,2'R)-107 (398 mg, 1.15 mmol, 70% yield) as a white solid. mp=185-186° C.; [α]−74° (c 1.08, CHCl$_3$); FTIR (neat): 2935, 2728, 2699, 1732, 1486, 1434, 1357, 1254, 1165, 1068, 1011 cm$^{-1}$; $^1$H NMR (500 MHz, free amine, CDCl$_3$) 7.52-7.38 (m, 4H), 6.09-6.01 (m, 1H), 5.65-5.60 (m, 1H), 4.33-4.21 (m, 1H), 3.70-3.59 m, 4H), 3.06-2.97 (m, 1H), 2.92-2.40 (m, 1H), 2.63-2.53 (m, 1H), 2.27-2.23 (m, 1H); $^{13}$C NMR (75 MHz, CDCl$_3$) 170.6 (C), 132.4 (CH), 131.5 (C), 131.2 (CH), 128.2 (CH), 123.0 (C), 121.9 (CH), 54.5 (CH), 53.1 (CH), 52.8 (CH$_3$), 41.5 (CH$_2$), 21.6 (CH$_2$), N—H proton not observed; LRMS (ESI) m/z (relative intensity): 310 (100); HRMS (ESI) calcd for C$_{14}$H$_{17}$BrNO$_2$ (MH$^+$-HCl): 310.0437. Found: 310.0431.

The above compound (2S,2'R)-107 was converted to the trifluoroacetamide in order to measure the enantiomeric excess. Pyridine (2 drops) and TFAA (2 drops) were added to a solution of the free amine (5 mg) in DCM (1 mL). The reaction mixture was stirred for 3 h. The solvent was removed under reduced pressure and the residue was purified by flash chromatography (SiO$_2$, EtOAc/Pentane=1:9) to give the amide. HPLC analysis (trifluoroacetamide): ee 95% (R,R-Whelk column, 3.0% i-PrOH in hexanes, 0.6 mL/min, λ=254 nm, t$_R$=23.2, minor; 31.2, major).

EXAMPLE 2

This Example demonstrates utility of the compounds.

Binding Studies

Binding of at biogenic amine transporters was determined using striatum and frontal cortex dissected from frozen Sprague-Dawley rat brains (Pel-Freez, Rogers, Ark.). Affinities of analogs at dopamine transport sites were determined by displacement of [$^{125}$I]RTI-55 binding in membranes from rat striatum, using 0.5 mg (original wet weight) of membranes and 10 pM [$^{125}$I]RTI-55. Non-specific binding was determined in the presence of 1 μM WF-23 (analog 3a). Affinities of analogs at 5-HT transport sites were determined by displacement of [$^3$H] paroxetine binding in membranes from rat frontal cortex, using 50 mg (original wet weight) of membranes and 0.4 nM [$^3$H]paroxetine. Non-specific binding was determined in the presence of 10 μM fluoxetine. Binding of analogs at norepinephrine transport sites was determined by displacement of [$^3$H]nisoxetine binding in membranes from rat forebrain, using 0.7 nM [$^3$H]nisoxetine. Non-specific binding was determined in the presence of 1 μM desipramine.

Potencies were calculated from displacement curves using 7-10 concentrations of unlabeled analogs, as analyzed by non-linear curve fitting. Because binding of tropanes at dopamine transporters is generally regarded as multiphasic,[3]

potencies in inhibiting [$^{125}$I]RTI-55 binding are reported as IC$_{50}$ values. For [$^3$H]paroxetine and [$^3$H]nisoxetine binding assays, K$_i$ values were calculated using the Cheng-Prusoff equation.[4] All data are mean values±S.E.M. of at least three separate experiments, each of which was conducted in triplicate.

Biological Activity

The binding affinities to dopamine (DA), serotonin (5-HT), and norepinephrine (NE) transporters for the series of compounds 4 were determined by standard methods (FIG. 1).

The compounds 4 displayed promising biological activity, many having good binding affinities to dopamine and norepinephrine transporters. Compounds binding to more than one monoamine transporter have been shown to be effective as antidepressants and so, the tetrahydropyridine derivatives 4 are expected to have similar activity.

The foregoing description of the specific embodiments is for the purpose of illustration and is not to be construed as restrictive. From the teachings of the present invention, those skilled in the art will recognize that various modifications and changes may be made without departing from the spirit of the invention.

I claim:

1. A composition comprising a compound having the following structure (2):

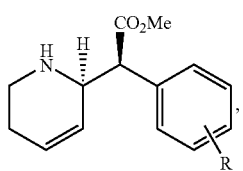

its enantiomer, or racemic mixtures thereof; wherein R can be such that the R-bearing ring is mono-, di- or tri-substituted, and in which each substituent is independently selected from the group consisting of substituted or unsubstituted phenyls, bromine, and chlorine.

2. The composition as in claim 1 wherein R is a p-bromo.
3. The composition as in claim 1 wherein R is a p-chloro.
4. The composition as in claim 1 wherein R is an unsubstituted p-phenyl.
5. The composition as in claim 1 wherein R consists of chlorine substituents at positions 3 and 4.
6. A composition comprising 1) a compound having the threo-diastereomeric structure of following structure (2):

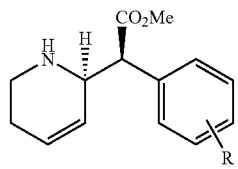

or a diastereomeric mixture of said threo-diastereomer and its erythro diastereomer; wherein R can be such that the R-bearing ring is mono-, di- or tri-substituted, and in which each substituent is independently selected from the group consisting of substituted or unsubstituted phenyls, bromine, and chlorine.

7. The composition as in claim 6 wherein R is a p-bromo.
8. The composition as in claim 6 wherein R is a p-chloro.
9. The composition as in claim 6 wherein R is an unsubstituted p-phenyl.
10. The composition as in claim 6 wherein R consists of chlorine substituents at positions 3 and 4.
11. A composition comprising a compound having the following structure:

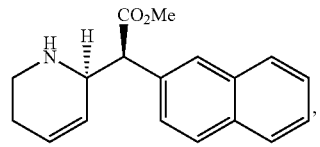

its enantiomer, or racemic mixtures thereof.

12. A composition comprising a compound having the threo-diastereomeric structure of following structure:

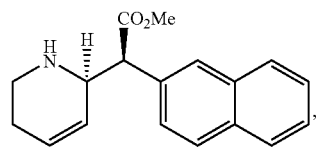

or a diastereomeric mixture of said threo-diastereomer and its erythro diastereomer.

* * * * *